United States Patent [19]

Crocco et al.

[11] Patent Number: 5,753,576
[45] Date of Patent: May 19, 1998

[54] REGENERATION OF A TITANIUM-CONTAINING MOLECULAR SIEVE

[75] Inventors: Guy L. Crocco, Wilmington, Del.; John G. Zajacek, Devon, Pa.

[73] Assignee: ARCO Chemical Technology, L.P., Greenville, Del.

[21] Appl. No.: 443,948

[22] Filed: May 18, 1995

[51] Int. Cl.$^6$ .............................. B01J 20/34; B01J 35/02; B01J 38/12

[52] U.S. Cl. .................................................. 502/38; 502/56

[58] Field of Search .................... 502/38, 56, 67

[56] References Cited

U.S. PATENT DOCUMENTS

| | | | |
|---|---|---|---|
| 4,833,260 | 5/1989 | Neri et al. | 549/531 |
| 5,374,747 | 12/1994 | Saxton et al. | 549/531 |
| 5,384,418 | 1/1995 | Zajacek et al. | 549/531 |
| 5,412,122 | 5/1995 | Saxton et al. | 549/531 |

FOREIGN PATENT DOCUMENTS

| | | | |
|---|---|---|---|
| 1249178 | 9/1989 | Japan | B01J 21/20 |
| 3-114536 | 5/1991 | Japan | B01J 21/20 |

OTHER PUBLICATIONS

"Synthesis of Propylene Oxide from Propylene and Hydrogen Peroxide Catalyzed by Titanium Silicalite", *Journal of Catalysis* 129, 159–167 (1991), by M.G. Clerici et al.

*Primary Examiner*—Glenn A. Caldarola
*Assistant Examiner*—Alexander G. Ghyka
*Attorney, Agent, or Firm*—Stephen D. Harper

[57] ABSTRACT

A titanium-containing molecular sieve which has been used as an oxidation catalyst is regenerated to provide a level of performance comparable to that of freshly prepared catalyst by heating at less than 400° C. in the presence of molecular oxygen. The same batch of catalyst thus may be used over an extended period of time in a continuous epoxidation process by periodic practice of the aforedescribed reactivation method.

16 Claims, No Drawings

REGENERATION OF A TITANIUM-CONTAINING MOLECULAR SIEVE

FIELD OF THE INVENTION

This invention relates to a method of restoring the activity and selectivity of a titanium-containing molecular sieve which has been used to catalyze an oxidation reaction such as the epoxidation of an olefin with hydrogen peroxide or other active oxygen species. Regeneration is accomplished by heating the spent catalyst at a moderately elevated temperature in the presence of air or other oxygen-containing gas.

BACKGROUND OF THE INVENTION

In recent years, various titanium-containing molecular sieves have been developed which usefully catalyze organic transformations such as the conversion of olefins to epoxides. For example U.S. Pat. No. 4,833,260 discloses the use of TS-1 titanium silicalite in epoxidation wherein hydrogen peroxide serves as a source of oxygen. Heterogeneous catalysts such as titanium silicalite are of great industrial interest, not only because of their high activity and selectivity, but also because such catalysts remain insoluble in liquid phase reaction mixtures and thus can be easily recovered and reused. It would be highly desirable to use titanium-containing molecular sieves in continuous processes. Unfortunately, such materials, for reasons which are not fully understood, tend to slowly deteriorate in performance when used for a long period of time. Due to the relatively high cost of synthesizing this type of catalyst, regeneration of the spent catalyst would be greatly preferred over replacement.

It has previously been proposed to regenerate used titanosilicate epoxidation catalysts by recalcining the catalysts at elevated temperatures. For example, G. Perego et al. *Proc. 7th Intern. Zeolite Confer.*, 1986, Tokyo, p. 827, discloses that a temperature of 550° C. is sufficient for this purpose. Subsequently, other investigators found that such regeneration could also be accomplished by baking the spent catalyst at temperatures of from 400° C. to 500° C. (Japanese Laid-Open Patent Application No. 3-114536). These investigators also concluded that temperatures lower than 400° C. would not be adequate to restore the activity of the catalyst.

SUMMARY OF THE INVENTION

We have now discovered that a spent titanium-containing molecular sieve may be reactivated by heating at a temperature of less than 400° C. but greater than 150° C. in the presence of molecular oxygen. The restoration in catalyst performance was unexpected and surprising in view of the express teaching of the prior art that such temperatures would be insufficient to regenerate catalysts of this type.

DETAILED DESCRIPTION OF THE INVENTION

The titanium-containing molecular sieves which may be regenerated using the process of this invention comprise the class of zeolitic substances wherein titanium atoms are substituted for a portion of the silicon atoms in the lattice framework of a molecular sieve. Such crystalline substances are well-known in the art.

Particularly preferred titanium-containing molecular sieves include the molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), "TS-3" (as described in Belgian Pat. No. 1,001, 038), "TS-48" (having a ZSM-48 structure), and "TS-12" (having an MTW-type structure). Also suitable for use are the titanium-containing molecular sieves having framework structures isomorphous to zeolite beta. The titanium-containing molecular sieves preferably contain no non-oxygen elements other than titanium and silica in the lattice framework, although minor amounts of boron, iron, aluminum, and the like may be present. Titanium-containing molecular sieves usable in the present regeneration process are sometimes referred to by workers in the field as "titanium silicalites", "titanosilicates", "titanium silicates", "silicon titanates" and the like. The molecular sieve may be admixed with a binder or other matrix material and may be in any physical form such as powder, pellets, granules, blocks, or the like.

Titanium-containing molecular sieves suitable for use in the process of this invention will generally have a composition corresponding to the following empirical formula $xTiO_2:(1-x)SiO_2$, where x is between 0.0001 and 0.500. More preferably, the value of x is from 0.01 to 0.125. The molar ratio of Si:Ti in the lattice framework of the titanium-containing molecular sieve is advantageously from 9.5:1 to 99:1 (most preferably, from 9.5:1 to 60:1). Large pore (mesoporous) as well as small pore (microporous) molecular sieves are suitable for use. Relatively titanium-rich molecular sieves may also be successfully regenerated. It has been found that spent titanium-containing molecular sieves typically are contaminated with organic substances, possibly polymeric or oligomeric in character, which are not present in fresh catalyst. The regeneration process herein described is capable of reducing the levels of such contaminants, as indicated by a decrease in the % C present by elemental analysis when heated at temperatures greater than 150° C.

Prior to regeneration, the titanium-containing molecular sieve will have been used to catalyze some desired synthetic process. The present method is particularly useful for restoring the activity and selectivity of a catalyst employed in olefin epoxidation. Such epoxidation processes are well-known (see, for example, U.S. Pat. Nos. 4,833,260, 5,354, 875, 5,262,550, 5,214,168, 5,374,747, 5,384,418, and 5,412, 122) and may be performed using a variety of olefins as well as different types of oxidizing agents. For example, the catalyst to be regenerated may have been recovered from a process wherein propylene is converted to propylene oxide using hydrogen peroxide. The regeneration method of this invention may also, however, be satisfactorily applied to deactivated titanium-containing molecular sieves utilized in other reactions such as, for example, hydroxylation of aromatic compounds, ammoximation of ketones, oxidation of saturated hydrocarbons to alcohols and ketones, and the like, including other oxidation processes.

The spent titanium-containing molecular sieve is preferably separated in solid form from any liquid components of the reaction mixture in which it may be present prior to regeneration. For example, where the molecular sieve has been deployed in the form of a slurry, it may be readily collected by filtration, centrifugation, decantation, or other such mechanical means and then transferred into a vessel which is suitable for carrying out the regeneration. Alternatively, where the molecular sieve has been used as a fixed bed, the liquid components may be simply drained or pumped away from the spent catalyst and regeneration conducted in the same vessel as the catalytic process. It is not, however, necessary to completely dry the recovered catalyst prior to regeneration since any minor amounts of solvent, reactants, and the like adsorbed on the catalyst can be readily removed and disposed of during such regeneration. An important advantage of the present method is that reactivation of catalyst may be performed in vessels of the type conventionally used for olefin epoxidation. Prior art regeneration processes utilizing calcination temperatures in excess of 400° C. may need to be carried out in specialized equipment fabricated using relatively high cost materials of construction in order to avoid metallurgical complications.

The spent titanium-containing molecular sieve is heated in the presence of molecular oxygen at a temperature greater than 150° C., but less than 400° C. The temperature range of from 165° C. to 360° C. is especially suitable. Due to the relatively low temperature at which the present process is operated, no significant loss in the crystallinity of the molecular sieve is observed. The temperature may be kept constant during regeneration or may be periodically or continuously increased or decreased as may be desired. The molecular oxygen may be combined with other gases such as nitrogen and the like; the use of air is especially advantageous due to the low costs associated with this source of oxygen. The process may be conducted such that a gas comprising molecular oxygen is passed over the titanium-containing molecular sieve in order to sweep away any volatile organic products evolved from the catalyst. Alternatively, the regeneration may be performed in a static manner. The catalyst is heated for such time as may be necessary to restore the desired level of activity and selectivity. Typical heating times are from 0.5 to 48 hours. The optimum time will vary somewhat depending upon the extent to which the catalyst has been deactivated, the type of reaction in which the catalyst has been used, the regeneration temperature, the flow rate of gas through the catalyst, as well as other factors, but may be readily ascertained by routine experimentation. A useful method of monitoring the extent of regeneration is to measure the %C present in the catalyst by elemental analysis. A spent catalyst will typically contain 1 weight % carbon or more, with a regenerated catalyst generally having less than 1 weight % carbon. Broadly speaking, it will usually be desirable to heat the spent catalyst under conditions effective to reduce the residual carbon level by at least 50% (more preferably, at least 75%) relative to the residual carbon level in the unregenerated catalyst. Activities and selectivities comparable to that of freshly prepared titanium-containing molecular sieves may be attained even with only relatively modest decreases in carbon levels however.

Following heat treatment, the regenerated molecular sieve may be further treated if so desired to further modify its catalytic properties. For example, the catalyst may be treated with a basic substance or a silylating agent to neutralize acidic sites which may be present. The regenerated catalyst may be admixed with freshly prepared catalyst prior to reuse, if so desired.

EXAMPLES

Examples 1–5

Titanium silicalite (TS-1), prepared using a literature procedure [*Zeolites*, 12, 943 (1992)], was sized to 18–30 mesh and packed in a fixed-bed propylene epoxidation reactor connected to propylene and hydrogen peroxide sources at the inlet and a back-pressure regulator at the outlet. Propylene and a hydrogen peroxide stream containing 81.8% isopropanol, 15% water, 3% hydrogen peroxide, 0.3% acetic acid, 0.02% formic acid, and 150 ppm ammonium acetate were passed over the catalyst for 1000 hours. Hydrogen peroxide conversion and propylene oxide selectivity (based on hydrogen peroxide) gradually decreased over the course of the run. The catalyst was removed from the reactor, analyzed for carbon and tested for reactivity in batch propylene epoxidation using a hydrogen peroxide stream comprised of 82% isopropanol, 15% water, 3% hydrogen peroxide, and 60 ppm ammonium dihydrogen phosphate (Table 1, Example 2). The hydrogen peroxide conversion and propylene oxide selectivity were significantly lower than for fresh catalyst tested in batch propylene epoxidation (Example 1). The spent catalyst was heated for 2 hours in air under static conditions at 250° C., 300° C., and 350° C. The carbon content of the catalyst decreased with increasing temperature, but in each case (Example 3–5) the activity and selectivity of the catalyst were restored to levels comparable to those observed using fresh catalyst (Example 1).

TABLE 1

| Regeneration Example # | 1 | 2 | 3 | 4 | 5 |
| --- | --- | --- | --- | --- | --- |
| Temp., °C. | fresh catalyst | — | 250 | 300 | 350 |
| % Residual Carbon | 0.0 | 4.8 | 0.87 | 0.46 | 0.17 |
| H$_2$O$_2$ Conversion % | 92 | 27 | 89 | 88 | 89 |
| Selectivities, % (based on H$_2$O$_2$) | | | | | |
| Propylene Oxide | 92 | 84 | 90 | 89 | 92 |
| Acetone | 4 | 4 | 4 | 4 | 4 |
| Glycols | 2 | 1 | 3 | 4 | 3 |
| Oxygen | 2 | 12 | 2 | 2 | 1 |

Examples 6–11

Titanium silicalite (TS-1) was prepared using the same literature procedure identified in Examples 1–5 and extruded using a silica binder. The extruded catalyst was loaded into a basket and placed in a CSTR to epoxidize propylene using a hydrogen peroxide stream containing 73% isopropanol, 24% water, 2.6% hydrogen peroxide, 0.3% acetic acid, 0.1% formic acid, and 80 ppm ammonium hydroxide. After 800 hours, the catalyst had lost considerable activity and was removed from the CSTR. The catalyst was analyzed for carbon content and tested for propylene epoxidation in a batch reactor using a hydrogen peroxide stream containing 74.6% isopropanol, 20% water, 5% hydrogen peroxide, 0.3% acetic acid, 01.% formic acid, and 78 ppm ammonium dihydrogen phosphate. The spent (unregenerated) catalyst gave much lower H$_2$O$_2$ conversion during a set reaction time (Table 2, Example 7) then fresh catalyst (Example 6). Different portions of the spent catalyst were heated under static air at temperatures ranging from 175° C. to 225° C. for periods of time ranging from 8 to 24 hours, reanalyzed for carbon content, and then tested again in batch propylene epoxidation runs. The results are summarized in Table 2 (Examples 8–11). In each case, the carbon content was reduced and the catalytic activity restored to levels comparable to freshly prepared catalyst.

TABLE 2

| Example # | 6 | 7 | 8 | 9 | 10 | 11 |
| --- | --- | --- | --- | --- | --- | --- |
| Regeneration Temperature, °C. | fresh catalyst | — | 225 | 200 | 200 | 175 |
| Regeneration | — | — | 8 | 8 | 24 | 24 |

TABLE 2-continued

| Example # | 6 | 7 | 8 | 9 | 10 | 11 |
|---|---|---|---|---|---|---|
| Time, hr. | 0.0 | 1.72 | 0.43 | 0.70 | 0.49 | 0.69 |
| % Residual Carbon | | | | | | |
| $H_2O_2$ Conversion % | 76 | 42 | 75 | 69 | 73 | 72 |
| Selectivities, % (based on $H_2O_2$) | | | | | | |
| Propylene Oxide | 90 | 86 | 87 | 87 | 87 | 87 |
| Acetone | 3 | 4 | 3 | 3 | 3 | 3 |
| Glycols | 6 | 9 | 9 | 9 | 9 | 9 |
| Oxygen | 1 | 1 | 1 | 1 | 1 | 1 |

Example 12

An extruded TS-1 catalyst (6.0 g), prepared as described above, was packed in a ⅜" tubular reactor. The reactor was connected to pumps for liquid propylene and hydrogen peroxide at the inlet and a back-pressure valve at the outlet. The reactor was heated to 60° C. using a circulating hot oil bath. Propylene and a hydrogen peroxide stream containing 81.8% isopropanol, 15% water, 3% hydrogen peroxide, 0.2% acetic acid, 0.02% formic acid, and 45 ppm diammonium hydrogen phosphate were pumped through the reactor at rates of 20 and 70 mL/h, respectively. The reaction initially gave 90% $H_2O_2$ conversion and 86% selectivity to propylene oxide. After 2040 hours, the conversion and selectivity had decreased to 39% and 77%, respectively. The feeds to the reactor were stopped and the catalyst heated in the reactor to 250° C. with a slight air flow for 8 hours. The epoxidation was then continued as described above to give 91% hydrogen peroxide conversion and 86% selectivity to propylene oxide.

We claim:

1. A method for regenerating a spent titanium-containing molecular sieve which has been used as a catalyst in an olefin epoxidation reaction comprising heating the spent titanium-containing molecular sieve at a temperature of less than 400° C. but greater than 150° C. in the presence of molecular oxygen for a time effective to restore the activity and selectivity of the spent titanium-containing molecular sieve to levels comparable to that of a freshly prepared titanium-containing molecular sieve.

2. The method of claim 1 wherein the spent titanium-containing molecular sieve has an MFI, MEL, or zeolite beta topology.

3. The method of claim 1 wherein a gas comprising molecular oxygen is passed over the spent titanium-containing molecular sieve during the regeneration.

4. The method of claim 1 wherein the regeneration is performed in a static manner.

5. The method of claim 1 wherein the spent titanium-containing molecular sieve has been used as a catalyst in a propylene epoxidation reaction.

6. The method of claim 1 wherein the temperature is from 165° C. to 360° C.

7. The method of claim 1 wherein the regeneration time is from 0.5 to 48 hours.

8. A method for regenerating a spent titanium-containing molecular sieve having an MFI, MEL, or zeolite beta topology which has been used as a catalyst in an olefin epoxidation reaction comprising heating the spent titanium-containing molecular sieve at a temperature of from 165° C. to 360° C. in the presence of molecular oxygen for a period of from 0.5 to 48 hours to restore the activity and selectivity of the spent titanium-containing molecular sieve to levels comparable to that of a freshly prepared titanium-containing molecular sieve.

9. The method of claim 8 wherein the spent titanium-containing molecular sieve has been deployed in the form of a fixed bed within a reactor vessel during said olefin epoxidation reaction.

10. The method of claim 9 wherein regeneration of the spent titanium-containing molecular sieve is performed within said reactor vessel.

11. The method of claim 8 comprising an additional subsequent step of treating the spent titanium-containing molecular sieve with a silylating agent.

12. The method of claim 8 wherein a gas comprising molecular oxygen is passed over the spent titanium-containing molecular sieve.

13. The method of claim 8 wherein the spent titanium-containing molecular sieve is in the form of a fixed bed during said heating.

14. The method of claim 8 wherein the spent titanium-containing molecular sieve is a TS-1 molecular sieve.

15. The method of claim 8 wherein the molecular oxygen is combined with another gas.

16. The method of claim 8 wherein air is used as a source of molecular oxygen.

* * * * *